United States Patent
Engqvist et al.

(10) Patent No.: US 9,445,900 B2
(45) Date of Patent: *Sep. 20, 2016

(54) IMPLANTS AND METHODS FOR CORRECTING TISSUE DEFECTS

(71) Applicant: OssDsign AB, Uppsala (SE)

(72) Inventors: Håkan Engqvist, Östhammar (SE); Thomas Engstrand, Uppsala (SE); Jonas Åberg, Hässelby (SE); Jan Bohlin, Harbo (SE)

(73) Assignee: OssDsign AB, Uppsala (SE)

(*) Notice: Subject to any disclaimer, the term of this patent is extended or adjusted under 35 U.S.C. 154(b) by 124 days.

This patent is subject to a terminal disclaimer.

(21) Appl. No.: 14/328,797

(22) Filed: Jul. 11, 2014

(65) Prior Publication Data

US 2014/0324187 A1    Oct. 30, 2014

Related U.S. Application Data

(63) Continuation of application No. 13/583,465, filed as application No. PCT/SE2011/050264 on Mar. 10, 2011, now Pat. No. 8,795,377.

(30) Foreign Application Priority Data

Mar. 10, 2010 (SE) .................................. 1000223
Nov. 5, 2010 (SE) .................................. 1051157

(51) Int. Cl.
*A61F 2/28*     (2006.01)
*A61B 17/80*    (2006.01)
*A61L 31/02*    (2006.01)
(Continued)

(52) U.S. Cl.
CPC ............. *A61F 2/28* (2013.01); *A61B 17/8085* (2013.01); *A61F 2/2875* (2013.01); *A61L 31/022* (2013.01); *A61L 31/026* (2013.01); *A61B 2017/00004* (2013.01); *A61B 2017/00526* (2013.01); *A61F 2/30965* (2013.01); *A61F 2002/3092* (2013.01);
(Continued)

(58) Field of Classification Search
CPC ...... A61F 2/28; A61F 2/2803; A61F 2/2805; A61F 2/2875; A61F 2/3099
See application file for complete search history.

(56) References Cited

U.S. PATENT DOCUMENTS 3,608,034 A    9/1971    Bramley et al.
4,905,679 A    3/1990    Morgan
(Continued)

FOREIGN PATENT DOCUMENTS

CN    1919357 A1    2/2002
CN    2607960 Y    3/2004
(Continued)

OTHER PUBLICATIONS

Bohner et al, J. Biomaterials, 26(33):6423-6429 (2005).
(Continued)

*Primary Examiner* — Jason-Dennis Stewart
(74) *Attorney, Agent, or Firm* — Porter Wright Morris & Arthur LLP

(57) ABSTRACT

An implant comprises a plurality of discrete biocompatible molded cement mosaic plates of maximum width w and thickness d connected by wire arms molded into and extending substantially laterally from the mosaic plates. Neighboring mosaic plates are separated by a gap of width t, and at least some of the mosaic plates have a hexagon shape.

20 Claims, 13 Drawing Sheets

(51) Int. Cl.
*A61F 2/30* (2006.01)
*A61B 17/00* (2006.01)

(52) U.S. Cl.
CPC .............. *A61F 2002/30143* (2013.01); *A61F 2002/30462* (2013.01)

(56) References Cited

U.S. PATENT DOCUMENTS

| | | |
|---|---|---|
| 5,152,836 A | 10/1992 | Hirano et al. |
| 5,338,356 A | 8/1994 | Hirano et al. |
| 5,368,602 A | 11/1994 | De la Torre |
| 5,468,242 A | 11/1995 | Reisberg |
| 5,503,164 A | 4/1996 | Friedman |
| 5,605,713 A | 2/1997 | Boltong |
| 5,683,667 A | 11/1997 | Fulmer et al. |
| 5,690,631 A | 11/1997 | Duncan et al. |
| 5,752,958 A | 5/1998 | Wellisz |
| 5,766,176 A | 6/1998 | Duncan |
| 5,782,971 A | 7/1998 | Constantz et al. |
| 5,783,217 A | 7/1998 | Lee et al. |
| 5,980,540 A | 11/1999 | Bruce |
| 5,984,925 A | 11/1999 | Apgar |
| 6,093,188 A | 7/2000 | Murray |
| 6,117,456 A | 9/2000 | Lee et al. |
| 6,206,957 B1 | 3/2001 | Wenz et al. |
| 6,338,810 B1 | 1/2002 | Carpena |
| 6,521,246 B2 | 2/2003 | Sapieszko et al. |
| 6,642,285 B1 | 11/2003 | Bohner et al. |
| 6,733,582 B1 | 5/2004 | Bohner et al. |
| 6,863,899 B2 | 3/2005 | Koblish et al. |
| 6,905,516 B1 | 6/2005 | Lemaitre et al. |
| 6,991,803 B2 | 1/2006 | Sapieszko et al. |
| 7,118,705 B2 | 10/2006 | Lin |
| 7,175,858 B2 | 2/2007 | Constantz et al. |
| 7,252,841 B2 | 8/2007 | Constantz et al. |
| 7,318,841 B2 | 1/2008 | Tofighi et al. |
| 7,351,280 B2 | 4/2008 | Khairoun et al. |
| 7,407,542 B2 | 8/2008 | Lemaitre et al. |
| 7,473,312 B2 | 1/2009 | Barralet et al. |
| 7,501,018 B2 | 3/2009 | Engqvist et al. |
| 7,655,047 B2 | 2/2010 | Swords |
| 7,709,029 B2 | 5/2010 | Chow et al. |
| 7,754,246 B2 | 7/2010 | Moseley et al. |
| 8,231,624 B1 | 7/2012 | Strippgen |
| 8,246,663 B2 | 8/2012 | Lovald et al. |
| 8,281,638 B2 | 10/2012 | Metzger |
| 8,282,396 B2 | 10/2012 | Chow et al. |
| 8,298,292 B2 | 10/2012 | Swords et al. |
| 8,361,126 B2 | 1/2013 | Perrow et al. |
| 8,366,751 B2 | 2/2013 | Pfefferle |
| 2003/0082232 A1 | 5/2003 | Lee et al. |
| 2003/0199615 A1 | 10/2003 | Chaput et al. |
| 2004/0250730 A1 | 12/2004 | Delaney et al. |
| 2005/0149032 A1 | 7/2005 | Vaughen et al. |
| 2005/0288790 A1 | 12/2005 | Swords |
| 2006/0039951 A1 | 2/2006 | Sapieszko et al. |
| 2006/0116682 A1 | 6/2006 | Longo |
| 2006/0224242 A1 | 10/2006 | Swords et al. |
| 2006/0235541 A1 | 10/2006 | Hodorek et al. |
| 2006/0235542 A1 | 10/2006 | Hodorek et al. |
| 2006/0239884 A1 | 10/2006 | Chane-Ching et al. |
| 2006/0263443 A1 | 11/2006 | Chow et al. |
| 2007/0092856 A1 | 4/2007 | Chow et al. |
| 2007/0189951 A1 | 8/2007 | Constantz et al. |
| 2008/0027455 A1 | 1/2008 | Boudeville |
| 2008/0028992 A1 | 2/2008 | Lee et al. |
| 2008/0187571 A1 | 8/2008 | Clineff et al. |
| 2008/0206300 A1 | 8/2008 | Bohner et al. |
| 2009/0022771 A1 | 1/2009 | Lynn et al. |
| 2009/0076617 A1 | 3/2009 | Ralph et al. |
| 2009/0220475 A1 | 9/2009 | Bohner et al. |
| 2010/0095870 A1 | 4/2010 | Insley et al. |
| 2010/0269736 A1 | 10/2010 | Chow et al. |
| 2010/0303888 A1 | 12/2010 | Barralet et al. |
| 2011/0014244 A1 | 1/2011 | Sapieszko et al. |
| 2011/0152195 A1 | 6/2011 | O'Mahony et al. |
| 2011/0158963 A1 | 6/2011 | Font Prez et al. |
| 2012/0058152 A1 | 3/2012 | Garcia de Castro Andrews et al. |
| 2013/0053900 A1 | 2/2013 | Qwarnstrom et al. |
| 2013/0066325 A1 | 3/2013 | Engqvist et al. |
| 2013/0138114 A1 | 5/2013 | Lin et al. |

FOREIGN PATENT DOCUMENTS

| | | |
|---|---|---|
| DE | 29913334 U1 | 9/1999 |
| EP | 005987 A1 | 12/1979 |
| EP | 543765 | 5/1993 |
| EP | 544384 B1 | 1/1996 |
| EP | 433852 B1 | 3/1996 |
| EP | 0654250 B1 | 12/1999 |
| EP | 1023032 B1 | 1/2002 |
| EP | 910993 B1 | 7/2002 |
| EP | 984745 B1 | 10/2003 |
| EP | 936929 B1 | 6/2004 |
| EP | 1380313 B1 | 5/2005 |
| EP | 1178847 B1 | 1/2007 |
| EP | 1905368 A1 | 4/2008 |
| EP | 1420725 B1 | 8/2008 |
| EP | 1958580 A1 | 8/2008 |
| EP | 2014258 A1 | 1/2009 |
| EP | 2030596 A1 | 3/2009 |
| EP | 1298103 B1 | 5/2011 |
| EP | 2474286 A1 | 7/2012 |
| EP | 2529702 A1 | 12/2012 |
| JP | 1-100049 A | 4/1989 |
| JP | 2-143945 U | 12/1990 |
| JP | 2006-218050 A | 8/2006 |
| JP | 2009-533177 A | 11/2010 |
| RU | 2074672 C1 | 3/1997 |
| RU | 2133593 C1 | 7/1999 |
| RU | 22032 U1 | 3/2002 |
| WO | 95/20368 A1 | 8/1995 |
| WO | 02/11781 A1 | 2/2002 |
| WO | 02/22045 A1 | 3/2002 |
| WO | 03/007831 A1 | 1/2003 |
| WO | 2004/093734 A2 | 11/2004 |
| WO | 2004/108019 A2 | 12/2004 |
| WO | 2004/112859 A1 | 12/2004 |
| WO | 2005/074453 A2 | 8/2005 |
| WO | 2005/077049 A2 | 8/2005 |
| WO | 2005/122956 A2 | 12/2005 |
| WO | 2007/047921 A2 | 4/2007 |
| WO | 2009/077210 A1 | 6/2009 |
| WO | 2010/055483 A2 | 5/2010 |
| WO | 2010/092001 A1 | 8/2010 |
| WO | 2011/009635 A1 | 1/2011 |
| WO | 2011/068451 A2 | 6/2011 |
| WO | 2012/016200 A1 | 2/2012 |
| WO | 2012/103164 A1 | 8/2012 |
| WO | 2012/118843 A1 | 9/2012 |
| WO | 2012/147114 A1 | 11/2012 |

OTHER PUBLICATIONS

Xu et al, Journal of Materials Science: Materials in Medicine, 18(7):1345-1353 (2007).
Barralet et al, J. Biomaterials, 25(11):2197-2203 (2004).
Habraken et al, Advance Drug Delivery Reviews, 59(4-5):234-248 (2007).
Han et al, Acta Biomaterialia, 5:3165-3177 (2009).
Desai et al, Advances in Bioceramics and Biocomposites II, Ceramic Engineering and Science Proceedings, vol. 27, Issue 6, Wereszczak et al, Editor, Wiley, pp. 61-69 (Nov. 2006).
Hirayama et al, Journal of Research of the National Institute of Standards and Technology, 113(6):311-320 (2008).
Official Action from corresponding Japanese Application 2012-557007 dated Jun. 10, 2014, and an English translation thereof.
Official Action and Search Report dated Jun. 27, 2014, and English translation thereof, from corresponding Chinese Application No. 2011800132880.
Supplemental Search Report dated Jul. 29, 2014 from corresponding European Application No. 11753693.8.

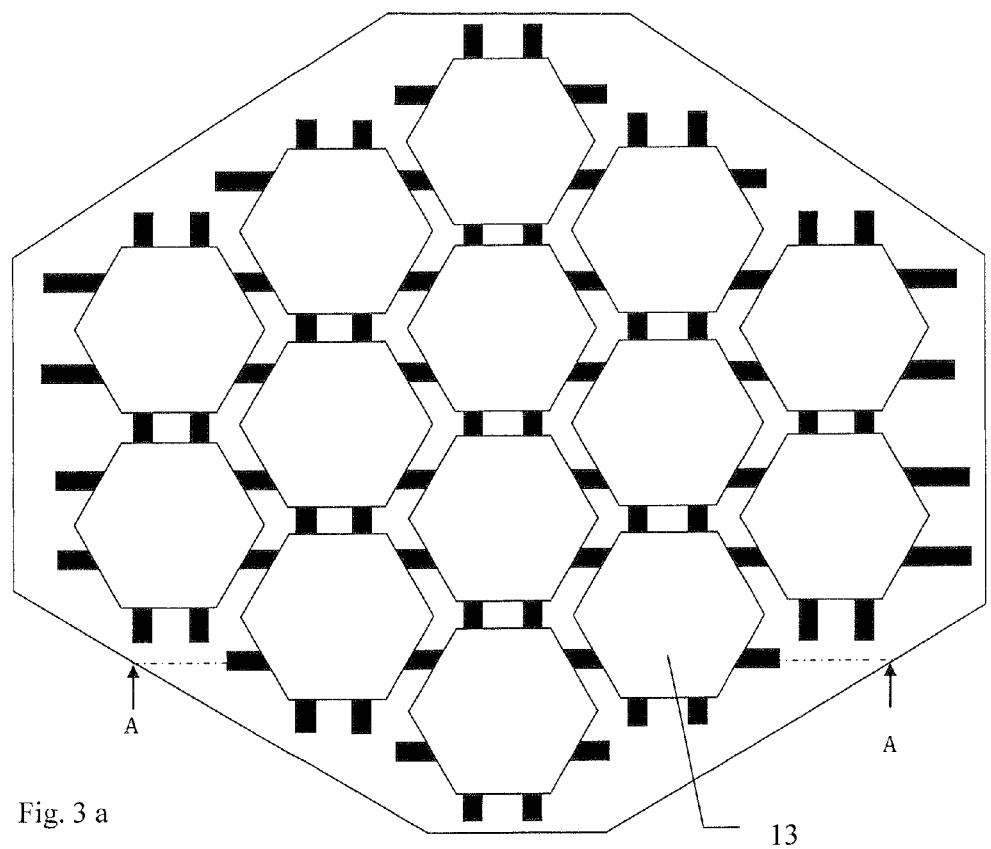
Fig. 3 a
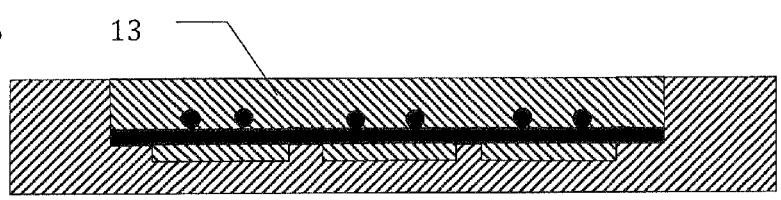
Fig. 3b    13
13

Fig 12a
Fig 12c
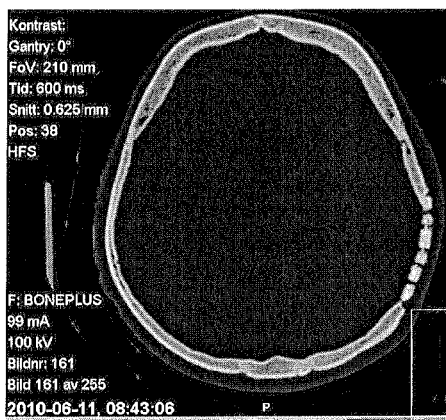
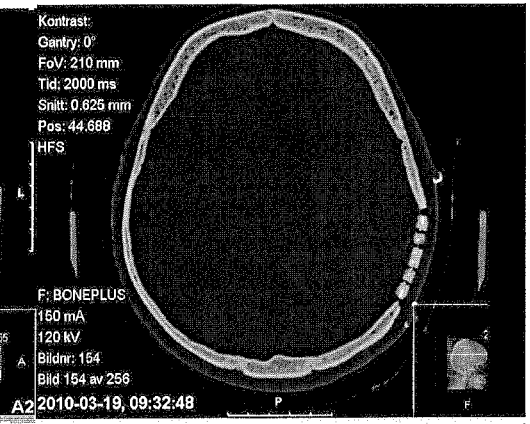
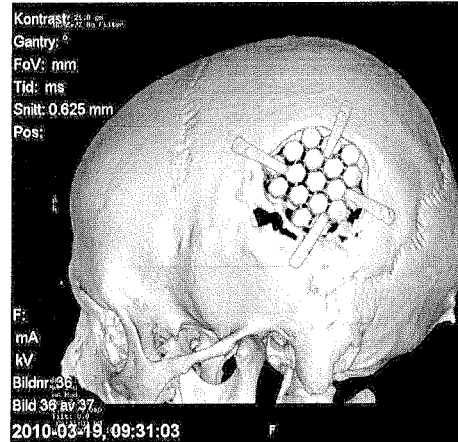
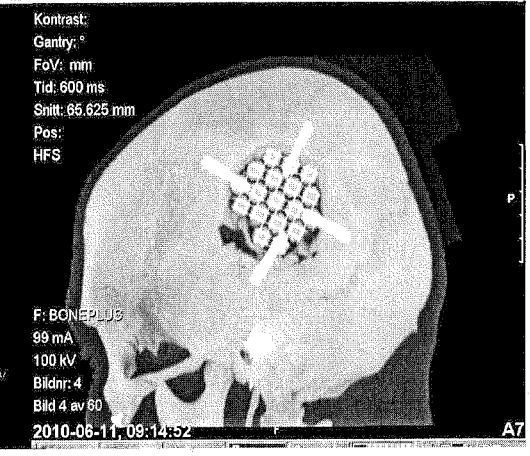
Fig 12b
Fig 12d

IMPLANTS AND METHODS FOR CORRECTING TISSUE DEFECTS

FIELD OF THE INVENTION

The invention relates to mosaic implants, methods for making such implants and methods for the correction of tissue defects.

BACKGROUND OF THE INVENTION

Bone tissue defects that cannot heal via tissue regeneration can be filled using autograph, allograph or synthetic scaffold materials. For large defects e.g. defects in the cranium or in long bones, healing of bone defect can be especially difficult. Scaffold strategies involve providing metal meshes or porous ceramic materials which new tissue can grow upon and/or into. Current strategies using metal mesh can give rise to problems with unhealed defects due to low new bone formation or infections. Currently used ceramics are mechanically weak and fragile which leads to a high risk of scaffold failure due to low mechanical strength. Metal meshes can be shaped in the operating theatre to closely fit the defect whereas the ceramics cannot be shaped after manufacturing and therefore have to be custom made in advance. To overcome the problem of low bone in-growth of Ti-meshes, coating a Ti-mesh with hydroxylapatite powder has been proposed for the use in revision surgery in joint replacement. This method increases the bone in-growth but limits the ability to shape the mesh in the operating theatre as bending the wires can cause the powder to fall off and the method has not been tested on other metals than Ti. There is unmet need for an implant system that facilitates bone in-growth, has high mechanical strength and has the ability to be shaped in the operating theatre.

BRIEF DESCRIPTION OF THE INVENTION

The present invention describes a mosaic implant, which can be used as a biomedical implant and which combines a wire or mesh anchoring system (a wire anchoring system comprises a plurality of wires, preferably crossing wires, where none of the wires are joined to each other while a mesh comprises at least two crossing wires joined at some or all of their intersections) and a biomaterial mosaic element, that can be shaped in the operating theatre and which provides increased combined bone in-growth and better mechanical properties compared to prior art systems. The implant comprises a mosaic element that combines at least one flexible high strength wire or mesh with at least two moulded solid mosaic plates. The invention can be employed for the correction of soft tissue defects and hard tissue defects. The biomaterial system can be composed of resorbable biomaterials and/or stable biomaterials such as polymers, ceramics and metals. Preferably the implant is osteo-conductive (i.e. can serve as a scaffold on which bone cells can attach, migrate, and grow and divide) or osteo-inductive (i.e. can serve to induce new bone formation), can be shaped in the operating room (OR) and have high mechanical strength. This is satisfied by using a mosaic structured implant system that combines a biomaterial anchoring system (for example a wire mesh) with a solid biomaterial system into a mosaic. This system has the beneficial effects of a mechanically strong wire mesh and an osteo-conductive and/or osteo-inductive solid part which means that the implant system can be easily shaped in the operation room by cutting the mesh into the desired geometrical shape and size. The solid plates, which are moulded at the intersections of the wires during manufacturing of the implant, are composed of an osteo-conductive and/or osteo-inductive material that facilitates bone in-growth onto the implant system.

Preferably the mesh is formed by intersecting wires to form a flat or a dished shape. In one embodiment of the present invention biomaterial mosaic plates are attached to intersections of the wire or mesh with a gap between the edge surfaces of adjacent plates. In this way a mosaic structure comprising wire-supported plates separated by gaps is formed. In another embodiment of the present invention a skin with a thickness which is less than the thickness of the biomaterial mosaic plates is formed between some or all of the mosaic plates. The skin is preferably frangible, and may be provided with lines of weakness, to allow selective breaking of it in order to shape the mosaic implant. Non-limiting examples of wires include polymers, shape memory alloys, Ti, Ti alloys (e.g. Ti6Al4V) and stainless steel. In the present application the word "wire" is intended to include filaments made of any such material. The biomaterials are preferably mouldable from the chemically bonded ceramic class of materials or a biopolymer, non-limiting examples include Ca-salts like: calcium sulphate, calcium phosphate, calcium silicate, calcium carbonate or combinations thereof. The materials are preferably moulded onto the wires or mesh using a non-aqueous water-miscible liquid or using a mixture of water and a non-aqueous water-miscible liquid, allowed to harden to form a mosaic implant in a water containing bath and subsequently the mosaic implant is released from the mould. After packing and sterilization the mosaic implant is ready to be used. The strength of the intersecting wires and, where present, the gaps between the plates are chosen so that a surgeon is able to shape the mosaic implant during an operation in order to adapt its shape to the tissue defect being corrected. The wider the gap between the plates the more the surgeon is able to deform the implant and hence produce a three-dimensional shape with complex curves. However wider gaps take longer to fill with bone tissue and in order to overcome this it problem while still allowing the formation of complex three-dimensional shapes it is possible to provide an implant with different gap widths between the plates—smaller gaps where the implant is intended to be substantially flat and wider gaps where the implant is intended to be curved.

BRIEF DESCRIPTION OF THE FIGURES

FIG. 3a) shows schematically the mould shown in FIGS. 1a) and 2a) after a second step in a method for manufacturing mosaic implant in accordance with the present invention;

FIG. 3b) shows schematically a cross-section though section C-C of the mould of FIG. 2a);

FIGS. 12a)-12d) show axial CT-scans (FIGS. 12a) and 12c)) and 3D-formatted CT-scans (FIGS. 12b) and 12d)) showing a mosaic implant covering the cranial bone defect in patient no 1 directly after surgery (FIGS. 12a) and 12b)) and 3 months later (FIGS. 12c) and 12d)); and, FIGS. 13a)-13d) show axial CT-scans (FIGS. 13a) and 13c)) and 3D-formatted CT-scans (FIGS. 13b) and 13d)) showing a mosaic implant covering the cranial bone defect in patient no 2 directly after surgery (FIGS. 13a) and 13b)) and 3 months later (FIGS. 13c) and 13d)).

DETAILED DESCRIPTION OF THE INVENTION

Figure 1A:
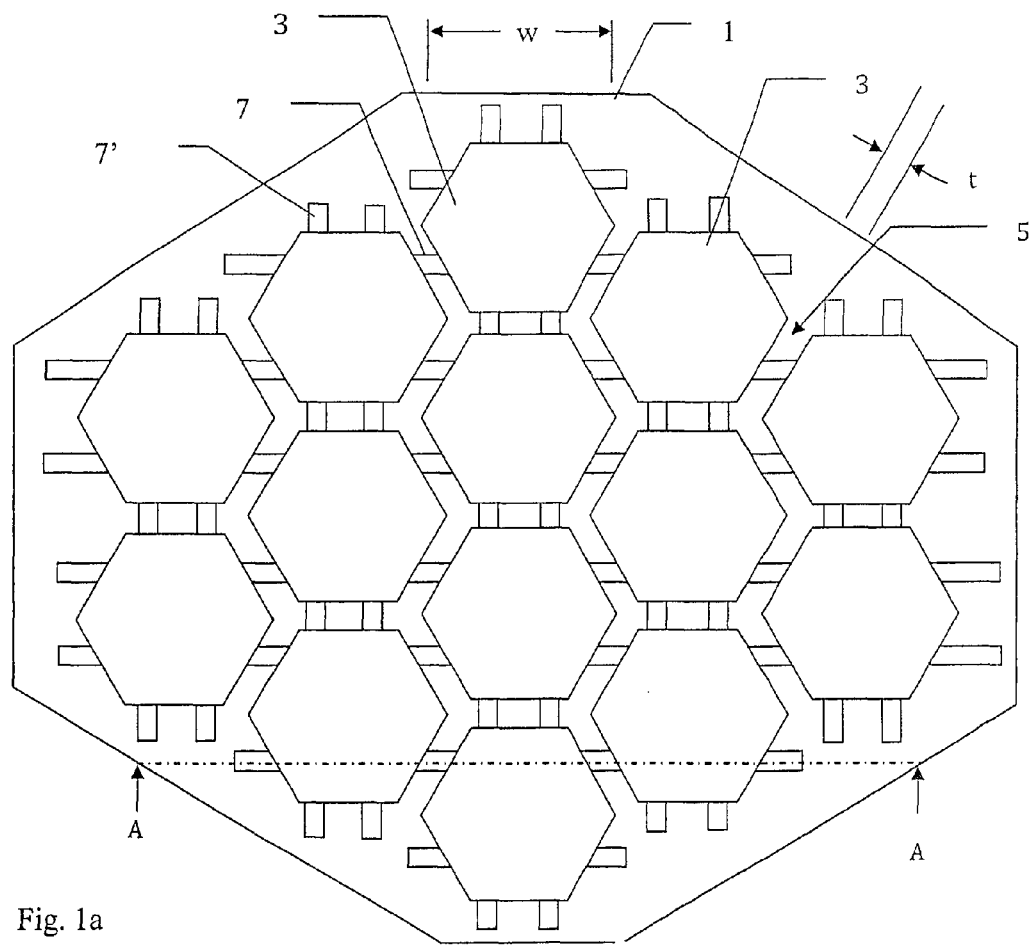
FIG. 1a) shows schematically a first embodiment of a mould for manufacturing a mosaic implant in accordance with the present invention.

In one embodiment of a method of manufacturing a mosaic implant in accordance with the present invention a mould 1 of depth D is used which, as shown in FIGS. 1a) and 1b), comprises a plurality of cavities 3 of depth d, each of which has the shape of a mosaic plate. The depth d of the cavities and the thickness of the resulting mosaic plate is less than the depth D of the mould. Each cavity 3 has a closed bottom end 3' which is closed by the floor 4 of the mould 1 and is open at the opposite open end 3" to allow filing of the cavity 3. Floor 4 does not have to be permanently attached to mould but may, for example, be a surface which the mould is in contact with during manufacturing of the implant and which can be removed after moulding to facilitate release of the implant from the mould Preferably each cavity and thus each mosaic plate subsequently formed in it has a regular shape such as a triangle, a square, a rectangle, a pentagon, a hexagon (as shown in FIGS. 1-4) etc with straight sides. Preferably all the cavities have the same shape. In the event that the shapes of cavities are not the same then adjacent cavities are preferably given complementary shapes such the cavities can be arranged in patterns with no overlapping and if desired can have substantially equal gaps between adjacent edges. The maximum width of each cavity and thus each mosaic plate is w and preferably the maximum width w of each cavity is greater than its depth d. Preferably w is between 2 and 20 millimeters, more preferably between 3 and 15 mm and even more preferably between 4 and 10 mm. Preferably d is between 10% and 150% of w, more preferably between 20% and 130% of w and most preferably between 50% and 130% of w. Each cavity is separated by a wall 5 of thickness t in the mould from its adjacent cavity/cavities. Wall thickness t in the mould leads to a gap of nominal thickness t between adjacent plates in the implant, is preferably less than 5 mm, more preferably less than 3 mm and most preferably less than 2 mm as the smaller the gap is then the easier it is for bone to grow and fill the gap between the mosaic plate. However the gap should not be too small as that will prevent adequate movement of the mosaic plates with respect to each other—a small gap means that after only a small deformation the walls of adjacent mosaic plates will collide and prevent the desired further shaping of the implant. In other words, having a larger gap allows the implant to be deformed more before adjacent plates contact each other, but the larger gaps between plates also take a longer time to fill with bone tissue or indeed may be impossible for the bone cells to bridge. It is of course possible to have different sized gaps between cavities if the implant is intended to have regions which while be substantially flat and other regions which will be formed into three-dimensional shapes. Each wall 5 between adjacent cavities 3 is pierced by at least one narrow, wire-retaining channel 7, 7' of width ww. These wire-retaining channels 7 are intended to receive and retain during the casting process the wires of similar width ww used to form a wire or mesh anchoring arrangement in the implant which maintains the mosaic plates in relationship to each other. An anchoring arrangement is preferably in the form of a mesh structure of crossing wires if the size of the implant is sufficiently large enough that it can accommodate a mesh structure. It is conceivable that with narrow, elongated implants the wires do not cross but are substantially parallel or that they only cross at a shallow angle and hence may only intersect in a portion of the cavities. Preferably the channels 7 running in a first direction have a depth d1 while channels 7' running in another direction, for example an orthogonal direction, have a depth d2 which shallower by a distance which is the same as, or less than the diameter of the wire (see below) used to form the mesh, i.e. $d1 > d2 \geq (d1-ww)$ so that crossing wires are close to each other or in contact with each other. In this embodiment of the invention the wires are arranged in a grid in which each wire is substantially parallel to its neighbouring wire(s) in the same plane and is crossed by, and in contact with, at least one perpendicular wire in a different plane. Preferably the wires are spaced such that each cavity is crossed by two substantially parallel wires running in a first direction and two wires running in a non-parallel direction e.g. the perpendicular direction. In another embodiment of the invention, not shown, each cavity is only crossed by one wire in the first direction and one wire in the perpendicular direction. This means that the subsequently formed implant can be lighter and more easily formed. It is also conceivable to have a plurality of wires which run substantially parallel in one direction through the cavity but which are crossed by a less number of wires, e.g. a cavity could have two parallel wires crossed by a single perpendicular wire. Other arrangements such as three wires crossing at 120° are also conceivable.

While the cavities have been shown with vertical walls 5, it is of course possible to have walls sloping such that the width across any section of the bottom closed end of each cavity is smaller than the width of the corresponding section of the open end of the cavity in order to form release slopes which aid releasing of the moulded product from the mould. Appropriately sloping walls also enable the implant to be deformed into deeper concave shapes without the edges of adjacent mosaic plates coming into contact with each other than otherwise is possible with vertical walls.

Figure 2A:
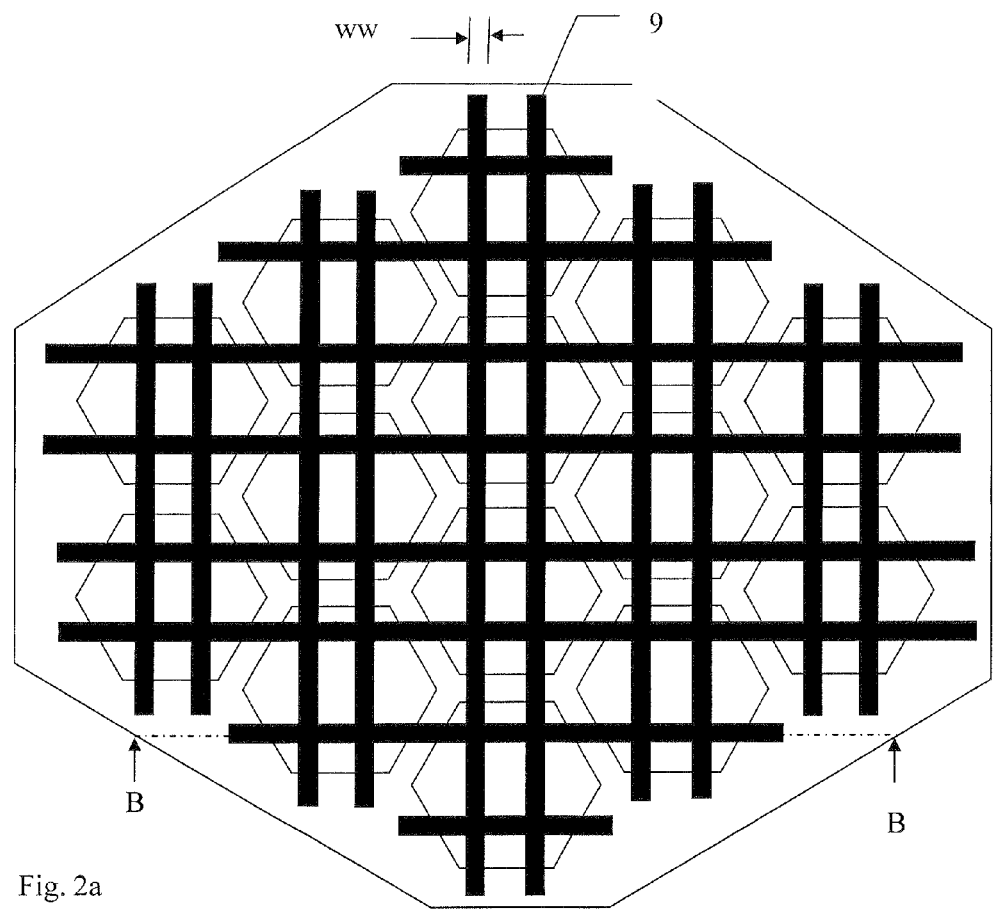
FIG. 2a) shows schematically the mould shown in FIG. 1a) after a first step in a method for manufacturing mosaic implant in accordance with the present invention.

FIGS. 2*a*) and 2*b*) shown the mould 1 in a first step in a method to manufacture a mosaic implant. In this step a wire mesh 11 is formed of overlapping wires 9, preferably of width or diameter ww so that they fit snugly in the wire-retaining channels in order to hold them in place during manufacturing and to reduce prevent leakage of cement around them. A wire is placed in, and preferably extends from end to end of, each of the channels. Preferably the channels 7 are arranged such that when the wires are arranged in them the central plane of the resulting wire mesh 11 lies on the central plane of the mould 1. This gives the advantage that when the mosaic implant is formed it is substantially symmetrical about the central plane of the wire mesh which means it is equally easy to make concave and convex adjustments to its shape. However in the event that it is desired to have an implant which is to be dished in only one direction, e.g. only convex then the wire mesh can be positioned further away from the central plane of the cavities to allow more bending in the desired direction before adjacent plates come into contact with each other.

FIGS. 3*a*) and 3*b*) shows the mould following a moulding step in the method for manufacturing a mosaic implant. In this step the cavities 3 are filled with a non-aqueous, hydraulic cement composition 13 which comprises a non-aqueous mixture of (a) a Ca-salt precursor powder composition, and (b) non-aqueous water-miscible liquid. This cement composition is moulded onto the wire mesh 11 and allowed to harden, in a wet to moist environment. The water in the environment displaces the non-aqueous water-miscible liquid from the hydraulic cement and allows the cement to harden. Preferably the temperature and amount of water in the environment are adapted so that the hardening process takes at least 24 hours as this leads to a strong product. Preferably before the cement has hardened fully, any excess cement composition 13 present in the wire-retaining channels 7, 7' is removed.

Figure 1B:
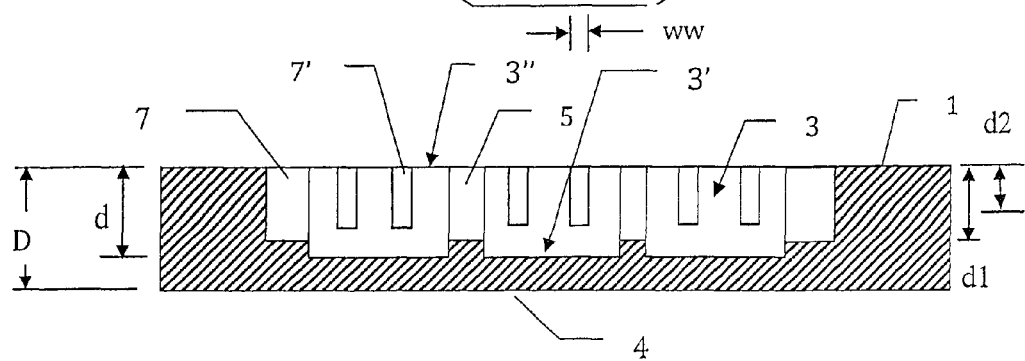
FIG. 1b) shows schematically a cross-section though section A-A of the mould of FIG. 1a)
Figure 2:
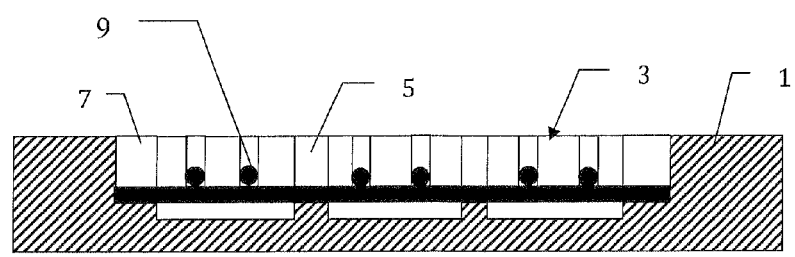
FIG. 2b) shows schematically a cross-section though section B-B of the mould of FIG. 2a)
Figure 4A:
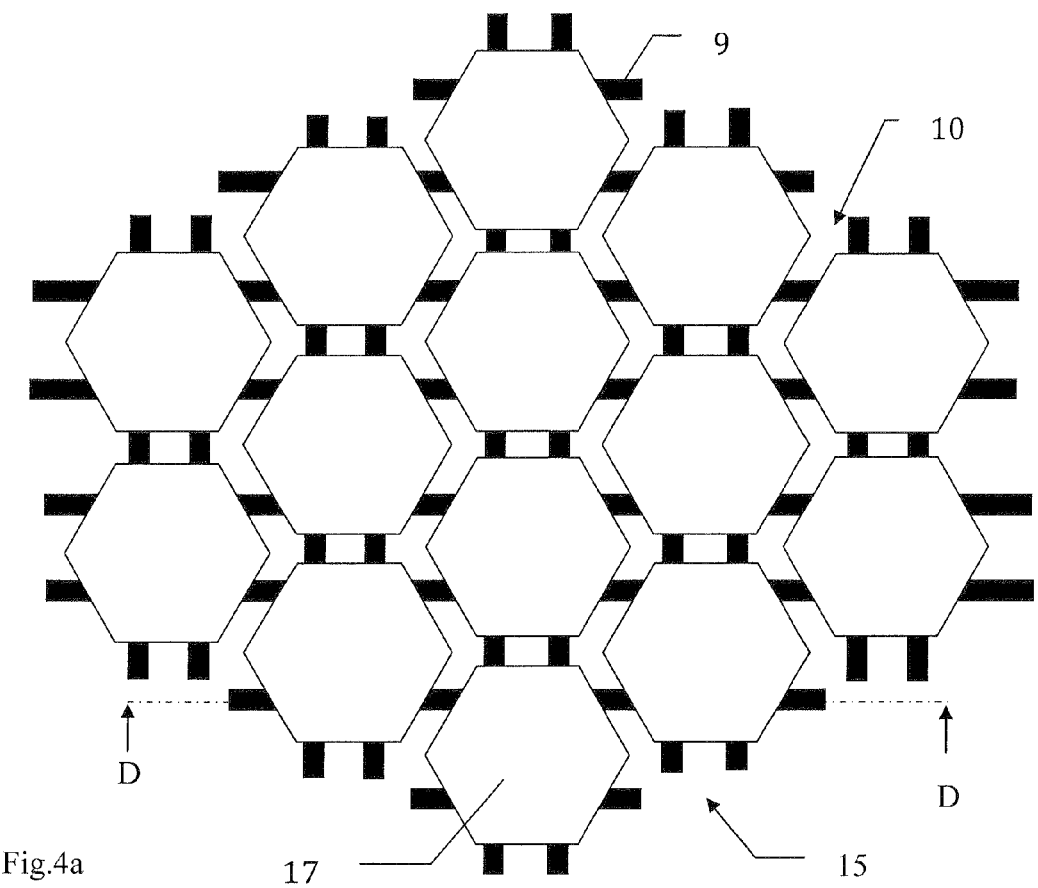
FIG. 4a) shows schematically a mosaic implant formed when using the mould shown in FIGS. 1-3 in a method for manufacturing mosaic implant in accordance with the present invention.
Figure 4B:
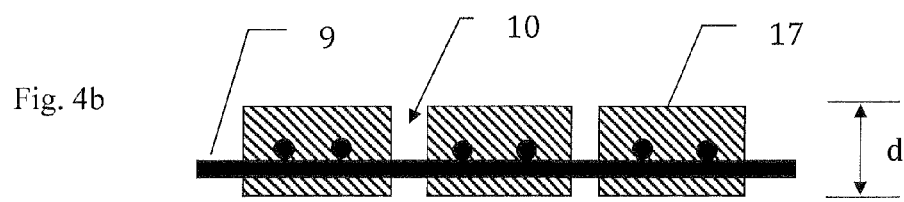
FIG. 4b) shows schematically a cross-section though section D-D of the mosaic implant of FIG. 4a)

FIG. 4*a*) shows schematically a mosaic implant 15 formed when using the mould shown in FIGS. 1-3 after it has been released from the mould 1. Mosaic implant 15 comprises a plurality of mosaic plates 17 each joined by wires 9 to adjacent mosaic plates while being separated from them by a gap 10 of width t. FIG. 4*b*) shows schematically a cross-section though section D-D of the mosaic implant of FIG. 4*a*).

Figure 5A:
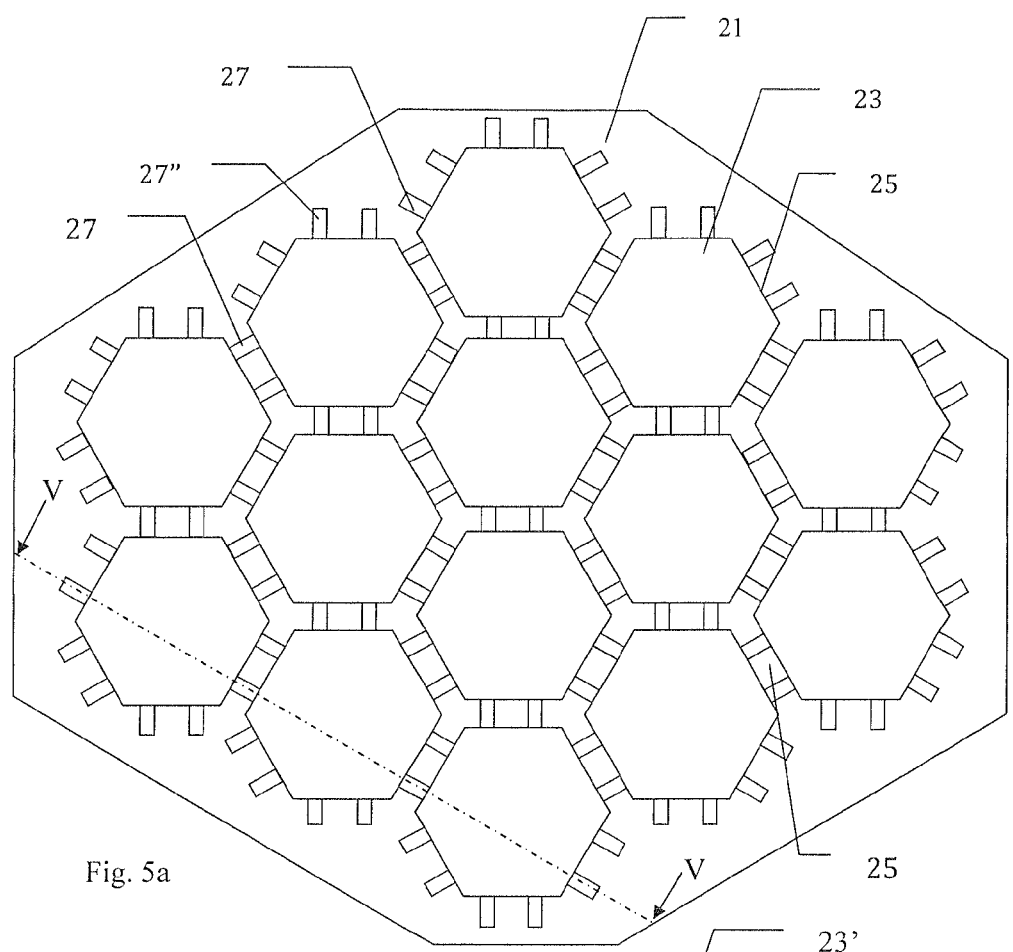
FIG. 5a) shows schematically a second embodiment of a mould for manufacturing a mosaic implant in accordance with the present invention.

In a further embodiment of a method of manufacturing an implant in accordance with the present invention a mould 21 of depth D is used which, as shown in FIGS. 5*a*) and 5*b*), comprises a plurality of cavities 23 of depth d, each of which has the shape of a mosaic plate. The depth d of the cavities is less than the depth D of the mould. Each cavity 23 has a closed bottom end 23' which is closed by the floor 24 of the mould 21 and is open at the opposite open end 23" to allow filing of the cavity 23. Each wall 25 between adjacent cavities 23 is pierced by at least one narrow, wire-retaining channel 27, 27' of width ww. In this embodiment first channels 27 running in a first direction piece two opposite walls of the cavity at a depth d1 while second channels 27' are aligned at an angle of 60° with respect to the first channels at a depth d2 which shallower by a distance which is the same as, or less than the diameter of the wire subsequently used to form the anchoring arrangement in the implant which maintains the mosaic plates in relationship to each other. These second channels piece two different opposing walls of each cavity. A third set of channels 27" is provided at an angle of 120° to the first set of channels 27 and at a depth of d3, and these piece the remaining two opposing walls of each hexagonal cavity. Thus in this embodiment of the invention the wires are arranged in a grid in which each wire is parallel to its neighbouring wire(s) and is crossed by at least two other wires which respectively make an angle of +60° and −60° with it. Preferably the wires are spaced such that each cavity wall is pierced by a pair of parallel wires. In another embodiment of the invention, not shown, each cavity wall is only pierced by one wire in the first direction and one wire in the perpendicular direction. This means that the subsequently formed implant can be lighter and more easily formed but at the cost of reduce strength and stability.

FIGS. 6*a*) and 6*b*) shown the mould 21 in a first step in a method to manufacture a mosaic implant. In this step a wire mesh 31 is formed of overlapping wires 29, preferably of width or diameter ww so that they fit snugly in the wire-retaining channels.

FIGS. 7*a*) and 7*b*) shows the mould following a moulding step in the method for manufacturing a mosaic implant. In this step the cavities 23 are filled with a non-aqueous, hydraulic cement composition 33. This cement composition is moulded onto the wire mesh 31 and allowed to harden, in a wet to moist environment. The water in the environment displaces the non-aqueous water-miscible liquid from the hydraulic cement and allows the cement to harden. Preferably the temperature and amount of water in the environment are adapted so that the hardening process takes at least 24 hours as this leads to a strong product. Preferably before the cement has harden fully, any excess cement composition 33 present in the wire-retaining channels 27, 27, 27''' is removed.

Figure 5B:
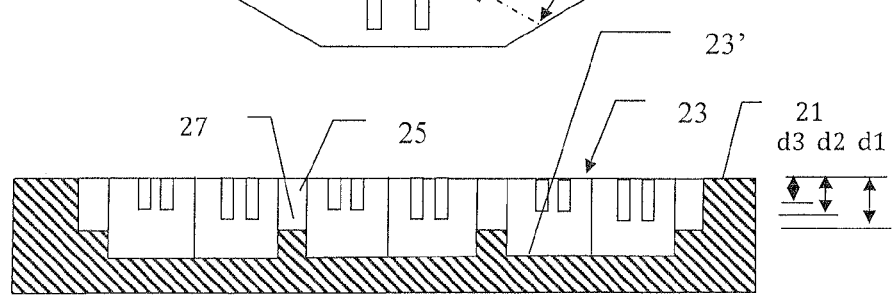
FIG. 5b) shows schematically a cross-section though section V-V of the mould of FIG. 5a)
Figure 6:
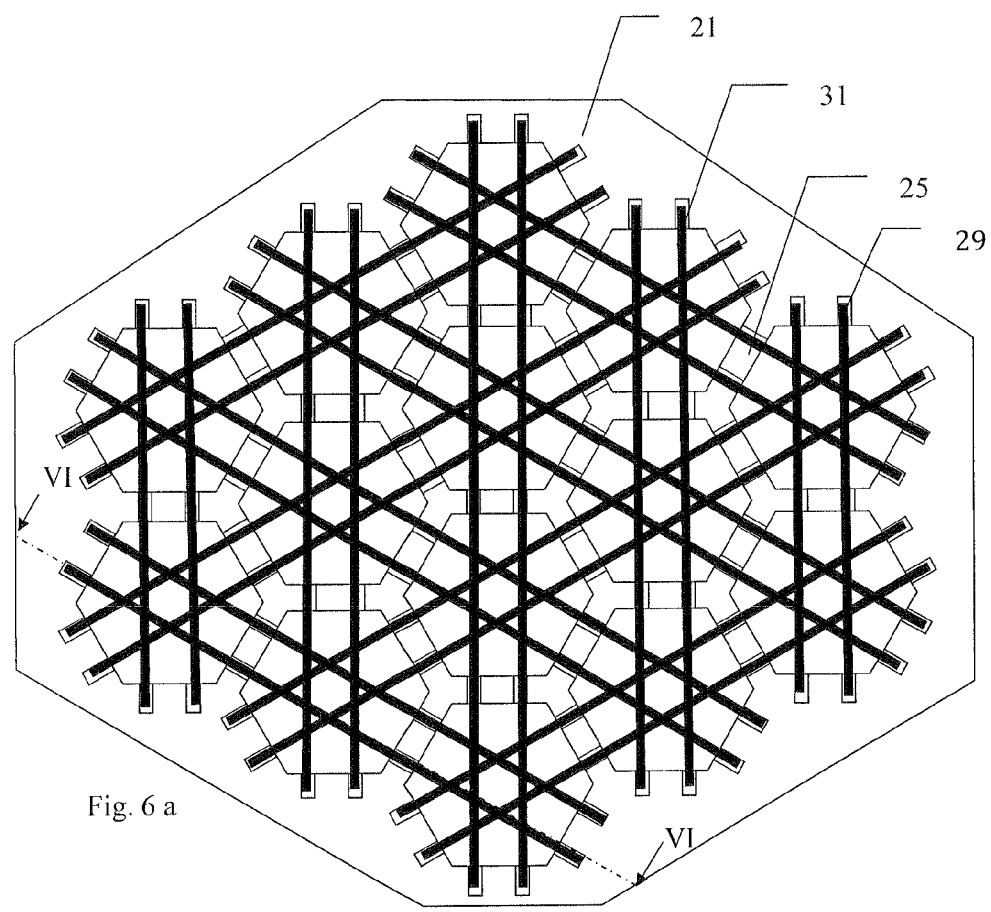
FIG. 6a) shows schematically the mould shown in FIG. 5a) after a first step in a method for manufacturing mosaic implant in accordance with the present invention.
FIG. 6b) shows schematically a cross-section though section VI-VI of the mould of FIG. 6a)
Figure 6:
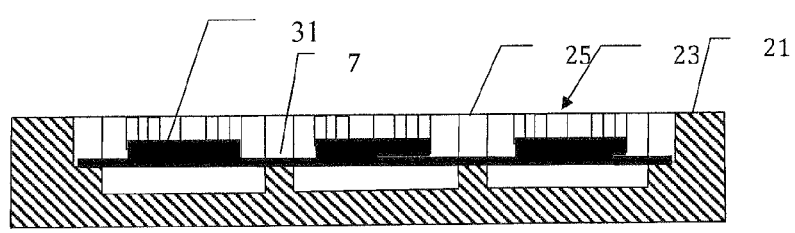
Figure 7:
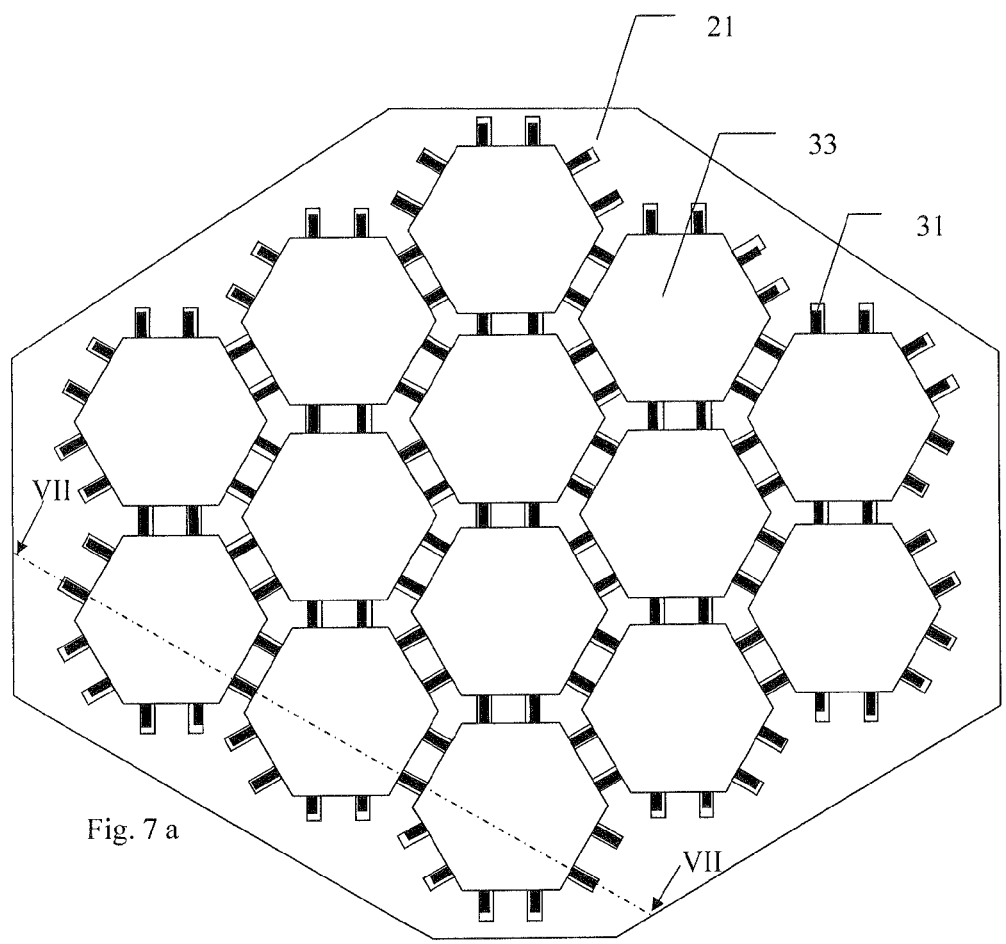
FIG. 7a) shows schematically the mould shown in FIGS. 5a) and 5a) after a second step in a method for manufacturing mosaic implant in accordance with the present invention.
FIG. 7b) shows schematically a cross-section though section VII-VII of the mould of FIG. 6a); and, FIG. 8a) shows schematically a mosaic implant formed when using the mould shown in FIGS. 5-7 in a method for manufacturing mosaic implant in accordance with the present invention.
Figure 7:
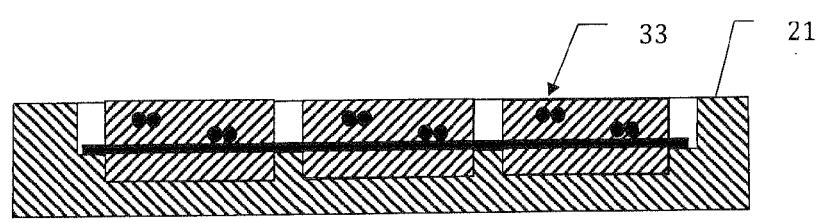
Figure 8:
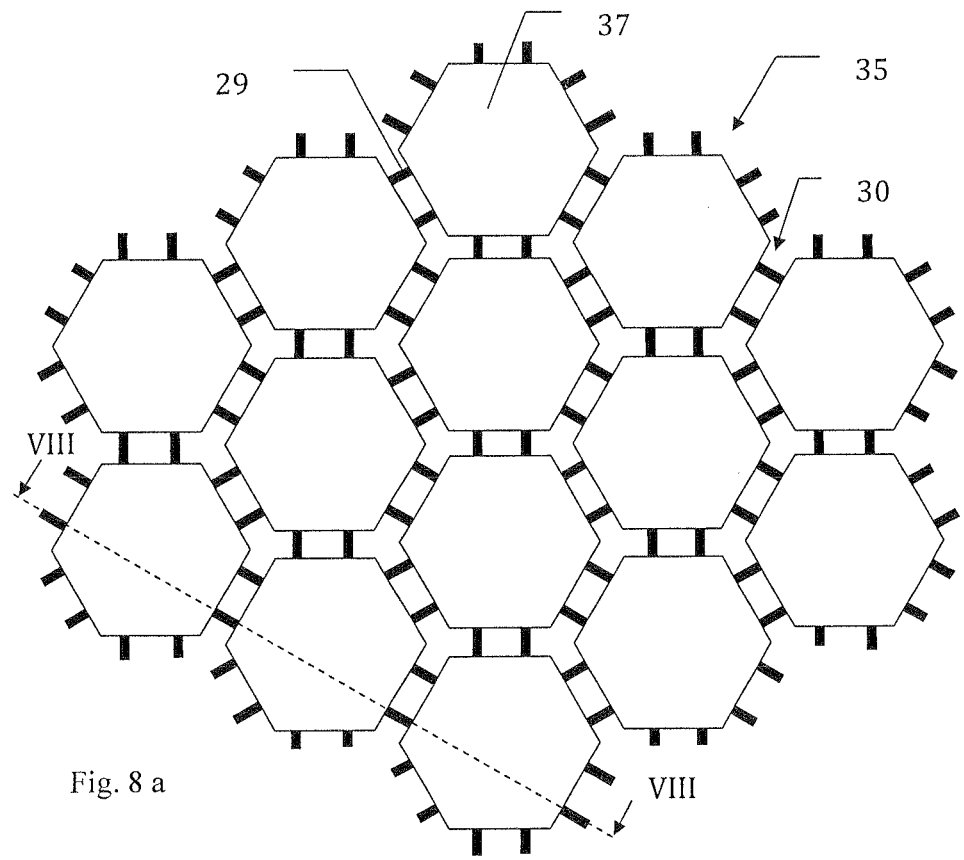
FIG. 8b) shows schematically a cross-section though section VIII-VIII of the mosaic implant of FIG. 8a)
Figure 8:
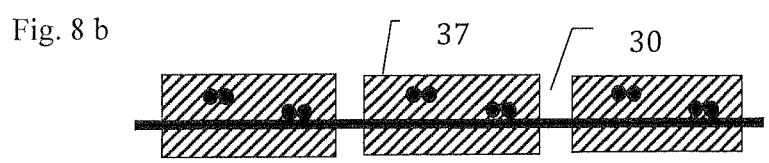

FIG. 8*a*) shows schematically a mosaic implant 35 formed when using the mould shown in FIGS. 5-7 after it has been released from the mould 21. Mosaic implant 35 comprises a plurality of mosaic plates 37 each joined by wires 29 to adjacent mosaic plates. FIG. 8*b*) shows schematically a cross-section though section VIII-VIII of the mosaic implant of FIG. 8*a*).

Figure 9A:
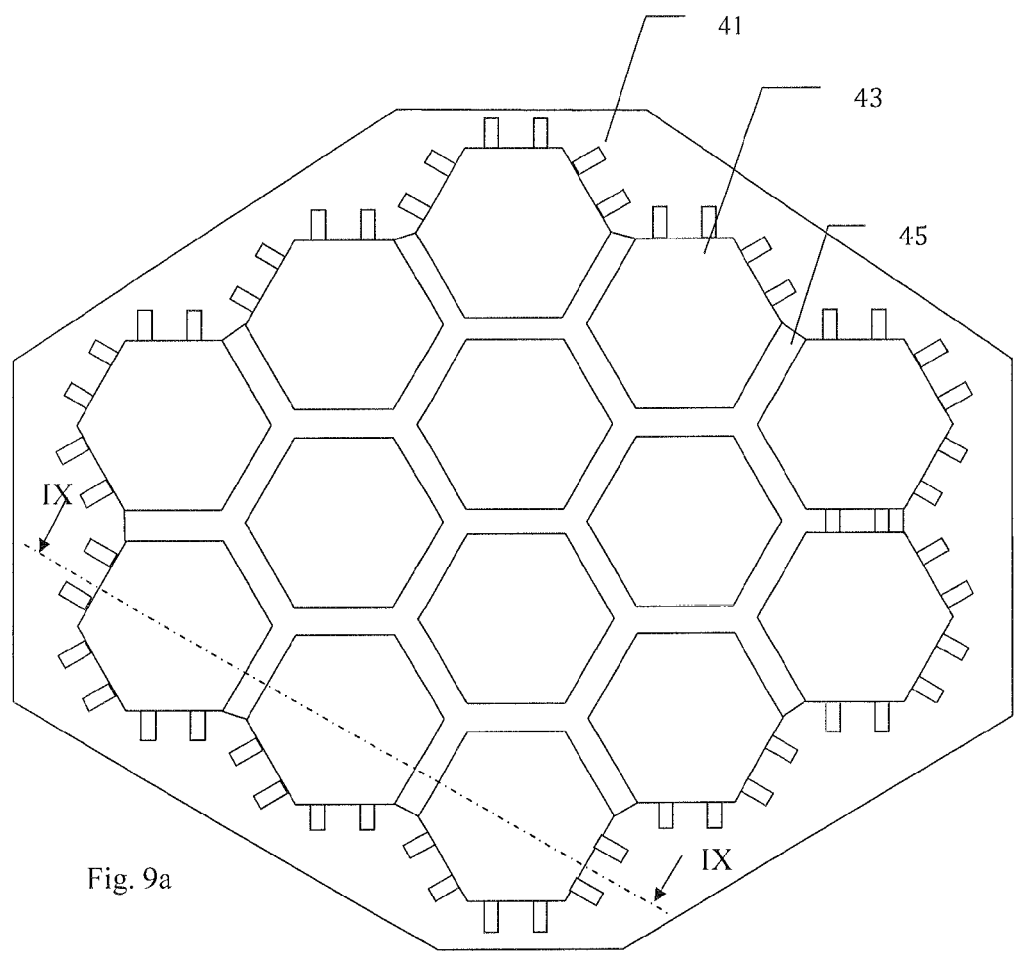
FIG. 9a) shows schematically a third embodiment of a mould for manufacturing a mosaic implant in accordance with the present invention.
Figure 9B:
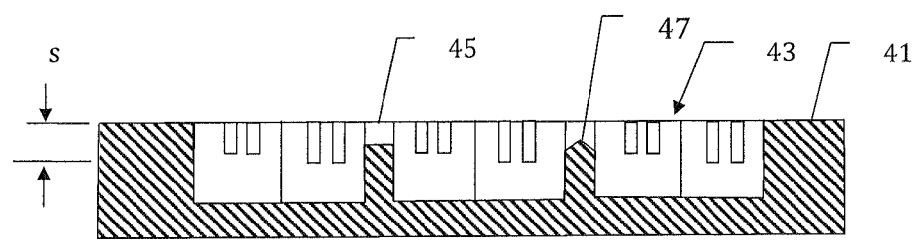
FIG. 9b) shows schematically a cross-section though section IX-IX of the mould of FIG. 9a)

FIGS. 9*a*) and 9*b*) show an example of a mould 41 for use in yet another embodiment of a method for manufacturing a mosaic implant in accordance with the present invention. In this embodiment of the invention it is desired to provide a bridging skin of cement material between adjacent mosaic plates. This skin preferably has a thickness s which is less than the thickness of the mosaic plates. Preferably it is more than 0.5 mm and less than 5 mm thick and is intended to strengthen the mosaic implant between mosaic plates. As such a skin would prevent the implant from being shaped, the skin is preferably made thin enough so that, if required, it can be broken or cut by a user in selected regions before being attached to a patient. By just breaking or cutting the skin of the implant at the places necessary to allow the implant to be deformed it is possible to form the implant to the desired shape while maintaining most of the increased strength provided by the skin. The skin can be formed by sinking the tops of the walls 45 between the cavities by a depth from the top surface of the mould 43 which is the same as the desired thickness of the skin. The tops of the walls may be provided with a ridge 47, preferably pointed, which causes local thinning in the subsequently formed skin. Wire-retaining channels are provided as necessary and once the wires have been placed in the channels the mould is filled with cement and allowed to set as before. In the event that wires are positioned at a depth which is lower than the desired bottom surface of the skin, spacer material can be provided above the wires to prevent excess cement material from filling the gap between the wires and the bottom surface of the skin.

Figure 10:
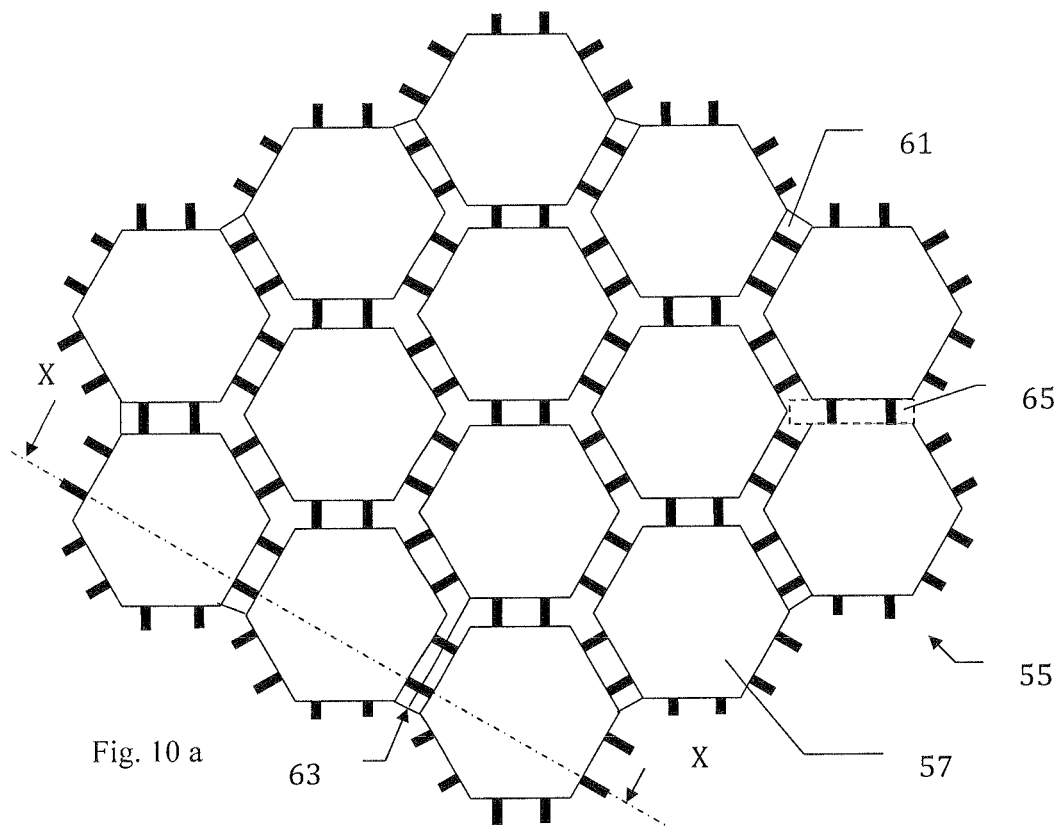
FIG. 10a) shows schematically a mosaic implant formed when using the mould shown in FIGS. 9a)-9b) in a method for manufacturing mosaic implant in accordance with the present invention.
FIG. 10b) shows schematically a cross-section though section X-X of the mosaic implant of FIG. 10a)
Figure 10:
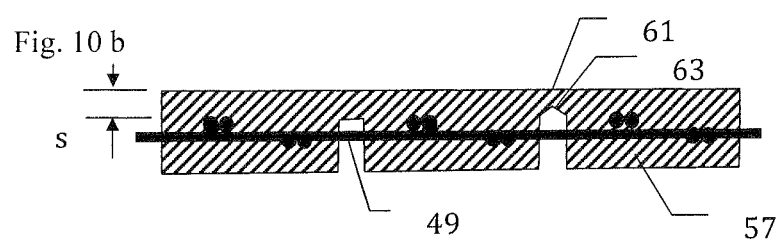

FIG. 10*a*) shows schematically from below a mosaic implant 55 formed when using the mould shown in FIGS. 9*a*) and 9*b*) after it has been released from the mould 41. Mosaic implant 55 comprises a plurality of mosaic plates 57 each joined by wires 49 and skin 61 of thickness s to adjacent mosaic plates. FIG. 10*b*) shows schematically a cross-section though section X-X of the mosaic implant of FIG. 10*a*). The part of the skin 61 where the ridges in the mould were placed is locally thinned, forming lines of weakness 63 which aid in fracturing the skin 61 when deformation of the implant is required.

In another embodiment of the present invention a mosaic implant comprises a plurality of mosaic plates, some of which are joined to one or more neighbouring mosaic plates by a skin and some of which are separated from one or more neighbouring plates by a gap (shown by dashed lines 65 in FIG. 10*a*).

Figure 11:
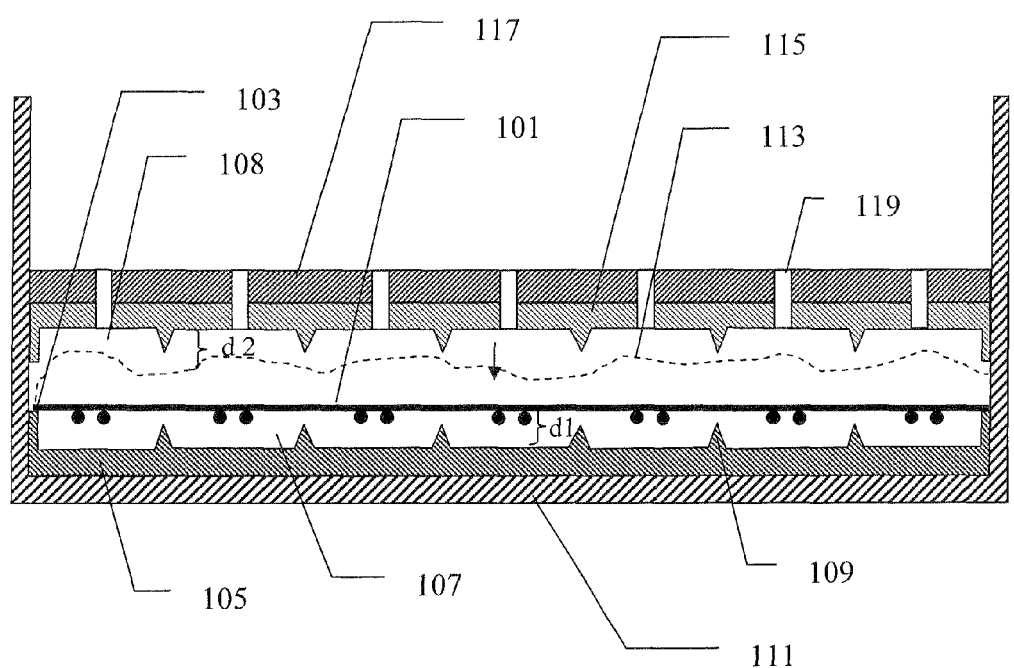
FIG. 11 shows schematically a cross-section though a further mould for manufacturing a mosaic implant in accordance with the present invention.

Other moulding methods may be used to form a mosaic implant in accordance with the present invention. For example, as shown schematically in FIG. 11, an interconnecting mesh 101 (or at least one wire) is placed on the exposed surface 103 of a first mould half 105 comprising a plurality of cavities 107 of depth d1 separated by walls 109. First mould half 105 is supported in a frame 111. First mould half 105 is provided with an excess amount of cement composition 113 (shown by dashed lines) which not only fills the cavities 107 and covers the mesh (or wire(s)) but also extends away from the exposed surface of the first mould half 105. A second mould half 115, which preferably has cavities 108 of depth d2 arranged as a mirror-image of the first mould half, is subsequently put on top of the mesh and compressed toward the bottom mould to allow moulding of mosaic plates around the interconnecting mesh. Second mould half 113 may be supported on a backing plate 117. The excess amount of cement composition should be sufficient to fill the cavities in the second mould half and should be positioned to be able to fill the second mould half. Excess cement is removed after the mould halves have been united and preferably before hardening of the cement. Hardening of the cement may be achieved by adding moisture via holes 119, each hole being connected to each moulding cavity within the mould. Holes 119 are also suitable for allowing excess cement to leave the mould.

The depths of the cavities in each mould half do not have to be the same. If they are different then the mesh or wire(s) will not be arranged on the central plane of the resulting implant which, if desired, will allow the implant to be used with the exposed mesh or wires further away from the skin of the patient and thus less likely to be damaged in the event of an accident.

The minimum number of cavities in each mould is two and there is no limit to the maximum number of cavities. The minimum number of wires is one, but preferably wires are at least provided as pairs of parallel wires to provide stability in the plane passing though the longitudinal axes of each pair of parallel wires.

In all embodiment of the present invention, depending on the composition of the cement, the hardening of the cement can be performed at reduced, or normal or elevated temperature, and in humid or wet environment. The mould may be may of any dimensionally-stable material which do not react negatively with the cement or mesh/wires. If the mould material is water-permeable it may assist in hardening of the cement.

There are three preferred options regarding the cement moulding:

1. Use (a) a Ca-salt precursor powder composition, and (b) non-aqueous water-miscible liquid. In this case the setting needs to be in a wet environment in order to initiate the hardening.
2. Use (a) a Ca-salt precursor powder composition, and (b) a mixture between water and a non-aqueous water-miscible liquid. Setting will initiate automatically but for final hardening a wet environment is needed.
3. (a) a Ca-salt precursor powder composition, and (b) water-based liquid. Hardening is initiated upon mixing. It is not necessary to perform hardening in a wet environment but hardening could be in a wet environment.

The Ca-salt precursor composition may comprise one or more Ca-salts selected from the group consisting of anhydrous dicalcium phosphate, dicalcium phosphate dihydrate, octacalcium phosphate, α-tricalcium phosphate, β-tricalcium phosphate, amorphous calcium phosphate, calcium-deficient hydroxyapatite, non-stoichiometric hydroxyapatite, tetracalcium phosphate and monocalcium phosphate monohydrate (MCPM), anhydrous monocalcium phosphate, phosphoric acid, pyrophosphoric acid, calcium sulphate (alfa or beta, preferably alfa) or calcium silicate (tricalciumsilicate, dicalciumsilicate or monocalcium silicate), calcium carbonate (aragonite, vaterite, calcite or amorphous) or combinations thereof.

In a first embodiment of the invention a non-aqueous water-miscible liquid may be used in preparing the pastes. Possible liquids include glycerol and related liquids compounds and derivates (substances derived from non-aqueous water-miscible substances), substitutes (substances where part of the chemical structure has been substituted with another chemical structure) and the like. The purpose of the non-aqueous water-miscible liquid is to give a longer working time during the moulding of the mosaic, because if the material starts to set then it is impossible to accurately achieve the mosaic shape.

Certain alcohols may also be suitable for use as such a liquid. Preferably the liquid is selected from glycerol, propylene glycol, polypropylene glycol), poly(ethylene glycol) and combinations thereof. The composition may also include agents that facilitate a fast diffusion of water into the paste in situ, preferably non-ionic surfactants like Polysorbates. The amount of surfactant is preferably between 0.01 and 5 wt % of the powder composition, most preferably 0.1-1 wt %.

In an alternate embodiment of the present invention the precursor powder composition is chosen to obtain a setting time above about 30 minutes and the liquid can then be water-based or water-containing. In this case the liquid can be pure water. In some formulations salts may be dissolved into the liquid to obtain a fast or slower setting, e.g. Citric acid, $H_3C_6H_5O_7$, Disodium pyrophosphate $Na_2H_2P_2O_7$, Sulfuric acid, $H_2SO_4$, phosphoric acid $H_3PO_4$. The hardening can then be performed in a dry environment.

The compositions may also include porogens to give a macroporous end product to facilitate fast resorption and tissue in-growth. The pores give a good foundation for bone cells to grow in. The porogen may include sugars and other fast-resorbing agents. The amount of porogen is suitably 5 and 30 wt % of the powder composition. This is regardless of whether the composition chosen above is premixed or not.

The compositions may also include a non-toxic gelling agent to enhance cohesiveness and washout resistance. The gelling agent may include collagen, gum, gelatin, alginate, cellulose, polyacrylic acid (e.g. PAA, PAMA), neutral polyacrylic acid (e.g. Na-PAA, Na-PAMA acid), HPMC, HMC and CMC and combinations thereof. The amount of gelling agent preferably represents between 0.1 wt % and 10 wt % of the powder composition, more preferably between 0.1 wt % and 2 wt %. This is regardless of whether the composition chosen above is premixed or not.

In all cement compositions selected above the precursor powder to liquid ratio should preferably be within the range of 1 and 10 as this gives optimal results. The mean grain size of the precursor powder is preferably below 100 micrometer, and more preferably below 30 micrometer as measured in the volumetric grain size mode. Smaller grain sizes give higher mechanical strength than larger grain sizes. However for the embodiment of the invention containing porous granules the granule size may be larger but preferably is still below 500 micrometer. Normally granules do not participate in the setting reaction of the paste. They are added as ballast to the material and the presence of pores gives a better biological response to the material. Preferably, at least some of the pores in a granule should be large enough for cells to enter into the granule, normally above at least 10 microns Inevitably there will also be smaller pores in the granules but they are of less importance for the cell integration.

In another embodiment of a method of manufacturing an implant in accordance with the present invention, in the moulding step a non-aqueous, hydraulic cement composition which comprises a non-aqueous mixture of (a) a Brushite- or Monetite-forming calcium phosphate powder composition, and (b) non-aqueous water-miscible liquid, is moulded onto the wire mesh and allowed to harden in a wet to moist environment.

In another embodiment of a method of manufacturing an implant in accordance with the present invention in the moulding step a non-aqueous, hydraulic cement composition which comprises a non-aqueous mixture of (a) a non-hydrated powder composition comprising porous β-tricalcium phosphate (β-TCP) granules and at least one additional calcium phosphate powder, and (b) non-aqueous water-miscible liquid, is moulded onto the wire mesh and allowed to harden in a wet to moist environment. An example of a wet environment is a water bath. An example of a moist environment is a chamber where the relative humidity is 100%. Optionally, hardening of the cement material can be performed at reduced, or normal or elevated temperature, combined with a humid, i.e. relative humidity over 50%, environment or wet environment.

In an alternate embodiment, the precursor powder composition is basic (apatitic) and comprises (a) a basic calcium phosphate component comprising porous β-TCP granules and tetra calcium phosphate (TTCP) and/or amorphous calcium phosphate, and (b) an acidic phosphate, non-limiting examples of which include monocalcium phosphate monohydrate (MCPM), anhydrous monocalcium phosphate, phosphoric acid, pyrophosphoric acid or combinations thereof. The components of the apatitic precursor powder compositions are chosen such that (i) the pH of the cement paste during setting is higher then 6; and (ii) the end-product of the setting reaction comprises amorphous calcium phosphate hydrate, hydroxyapatite, ion-substituted hydroxyapatite, or combinations thereof.

Once the cement has hardened the cement and wire construction can be removed form the mould, any unwanted cement, for example cement that has fastened onto the wires between the hexagonal plates 15, removed and the implant packaged and sterilized.

Optionally the cement and wire construction of the implant system of the present invention could be exposed to pressure during hardening, for example by pressing an inverse mould against the cement, in order to obtain a stronger end product.

Optionally the implant system of the present invention can be combined with drugs to form a drug delivery system. Examples of drugs are anti-inflammatory, antibiotics, pain-killers, anti cancer drugs, bone growth promoting agents, fibroblast growth factors and bisphosphonates. These drugs can be delivered by using porous components in the implant system, e.g. porous wires or porous cement or porous granules or a porous coating, and introducing the drugs into the pores of the porous component.

The implant system can be attached to the host tissue via sutures and/or plates and screws and/or clamps or any other fixing means.

The implant system can be used in tissue replacements (bone and soft tissue replacement) and in veterinary medicine. For soft tissue replacement the mosaic structure is preferably composed of polymeric materials, preferably resorbable polymers. For hard tissue the mosaic system is preferable composed of metal wires and ceramic solids, preferably of metal wires and resorbable ceramics. In the event that the patient is still growing it is appropriate to use resorbable materials for the wires and/or the mosaic plates. Suitable resorbable polymers are Polydioxanone, poly L-lactic acid, and polyglycolic acid.

The implant system may also optionally be combined with an injectable biomaterial or drug delivery vehicle that guides the tissue in-growth into the gaps between the plates in the system.

Experimental Example 1

A mosaic implant was manufactured using the manufacturing method described above using premixed acidic calcium phosphate cement moulded onto Ti wires. The clinical use of this example of a mosaic implant was for the restoration of a large cranial defect. Wires were placed in the mould which was then filled with the premixed acidic calcium phosphate cement and allowed to harden in water for 48 hours at 20 degrees C.

The premixed acidic calcium phosphate cement consisted of beta-tricalcium phosphate, mono calcium phosphate monohydrate and glycerol. The beta-tricalcium phosphate and mono calcium phosphate monohydrate was mixed in a molar ratio of 1:1 and the glycerol was added to the powder to obtain a powder:liquid ratio of 3.9:1 [g/ml]. The cement was thoroughly mixed until a homogenous paste was formed.

After hardening the cement was found to consist of mainly the two phases brushite ($CaHPO_4\text{-}2H_2O$) and monetite ($CaHPO_4$)—however some calcium pyrophosphate ($Ca_2O_7P_2$) was also found.

The mosaic implant was released from the mould, packaged and steam sterilized. The manufactured mosaic structure was evaluated clinically.

Clinical Evaluation

Patient no 1: A 22-year old patient with a parietal cranial bone defect measuring 40×40 mm was operated on. The defect was exposed through a local cranial skin flap. A sterilized mosaic implant with original size of 100×100 mm was cut using a wire cutter and adjusted to a size of approximately 45×45 mm. The mosaic implant was fitted into the defect, which required cutting away small amounts of adjacent cranial bone to ensure a good fit. The periphery of the defect was formed to make a ledge which supported the implant and the implant was subsequently clamped to the ledge by titanium plates and screws. The patient demonstrated no local or systemic side effects and could leave the hospital the day after surgery. A postoperative CT-scan (see FIGS. 12a) and 12b)) demonstrated the implant in perfect position covering the original bone defect. The clinical and radiological follow-up made 3 months after surgery revealed a well-tolerated implant without signs of infection, inflammation or penetration through the skin. The implant was still intact without resorption at this early time-point as demonstrated by CT-scans shown in FIGS. 12c) and 12d)).

Figures 13A, 13B, 13C, 13D:
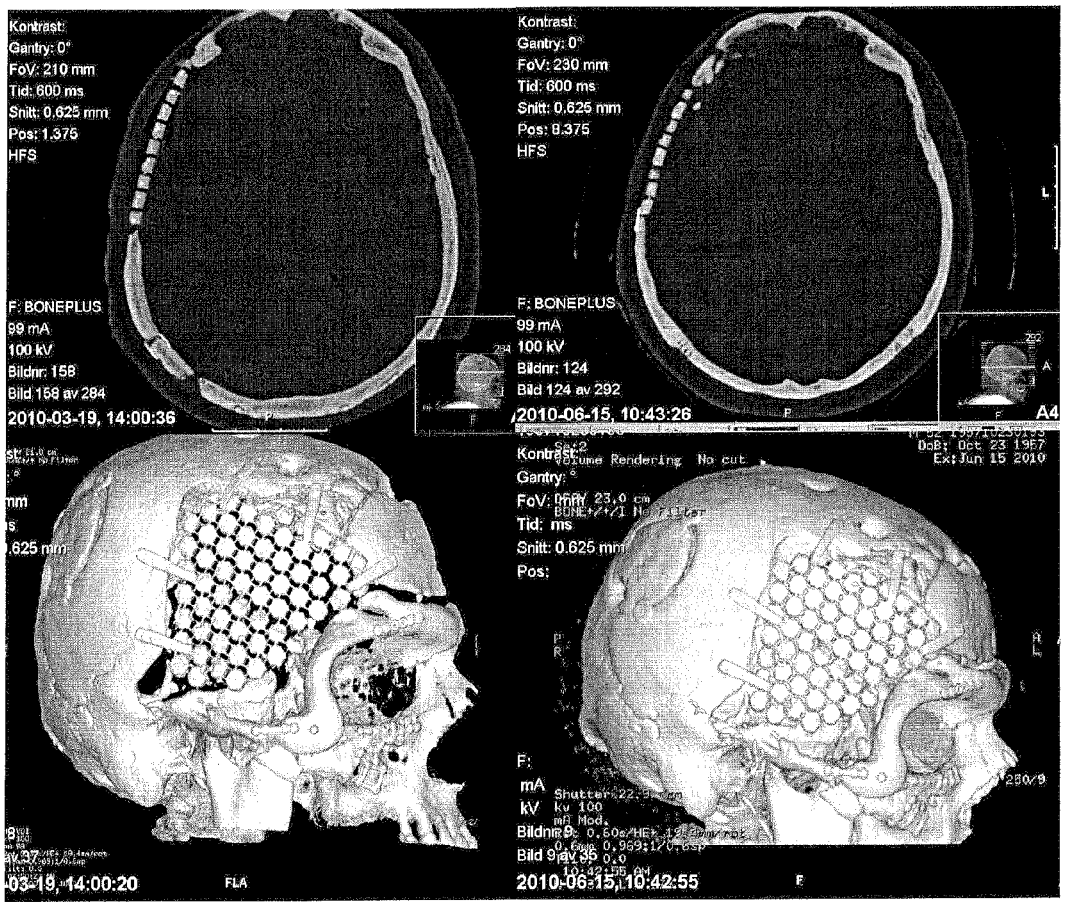

Patient no 2: A 53-year old smoking patient had a large temporal cranial bone defect measuring 80×90 mm. The patient was previously extensively operated on due to the complex cranio facial trauma and has suffered previous implants that failed due to infections and penetration through the skin. The bone defect was exposed through a standard bi-coronar cranial skin flap. The soft tissue covering the defect was mainly fibrotic. A sterilized mosaic implant with original size of 100×100 mm was cut using wire cutters and adjusted to a size of approximately 85×95 mm. The mosaic implant was fitted into the defect by cutting adjacent cranial bone to form supporting ledges and the implant was subsequently attached by clamping the implant between the ledges and titanium plates and screws. The patient demonstrated a mild local reaction at the operation site that eventually declined 3-4 days after surgery. A postoperative CT-scan demonstrated the implant in perfect position covering the original bone defect as can be seen in FIGS. 13a) and 13b). Clinical and radiological follow-up 3 months after surgery show a well-tolerated implant without signs of infection, inflammation or penetration through the skin. The implant was still intact without resorption at this time-point as demonstrated by CT-scans shown in FIGS. 13c) and 13d).

While the implant was attached using clamps in the above examples it is also possible to attach it using sutures and a combination of clamps and sutures.

The invention is not limited to the embodiments shown, which can be varied freely within the framework of the following claims. In particular, the features of the various embodiments and examples described may be freely combined with each other in order to reach additional embodiments, which are all considered part of the scope of the present application.

The invention claimed is:

1. An implant, comprising a plurality of discrete biocompatible molded cement mosaic plates of maximum width w and thickness d connected by wire arms molded into and extending substantially laterally from the mosaic plates, wherein neighbouring mosaic plates are separated by a gap of width t, and wherein at least some of the mosaic plates have a hexagon shape.

2. An implant according to claim 1, wherein each mosaic plate has a maximum width w which is between 2 and 20 millimeters.

3. An implant according to claim 2, wherein each mosaic plate has a maximum width w between 3 and 15 mm.

4. An implant according to claim 2, wherein each mosaic plate has a maximum width w between 4 and 10 mm.

5. An implant according to claim 2, wherein the maximum width w is greater than the thickness d.

6. An implant according to claim 5, wherein t is less than 3 mm.

7. An implant according to claim 6, wherein the molded cement mosaic plates comprise Monetite.

8. An implant according to claim 1, wherein the molded cement mosaic plates comprise Monetite.

9. An implant according to claim 8, wherein the mosaic plates comprising Monetite are formed from an acidic cement composition comprising beta-tricalcium phosphate and monocalcium phosphate monohydrate.

10. An implant according to claim 1, wherein the wire arms are formed of titanium or titanium alloy.

11. An implant according to claim 1, wherein the wire arms are formed of polymer.

12. An implant according to claim 1, wherein at least some of the hexagonal shaped mosaic plates have slanted side walls whereby, in each plate having slanted side walls, a maximum width w of a top hexagonal-shaped surface of the plate is greater than a maximum width w of a bottom hexagonal-shaped surface of the plate.

13. A method of implanting the implant of claim 1 in a patient, comprising the steps of:
  i) exposing at least some of the tissue of the patient surrounding the area where the implant is to be placed,
  ii) attaching the implant to tissue, and
  iv) closing the exposure.

14. A method according to claim 13, wherein the step of attaching the implant to the tissue is achieved by using sutures, clamps, screws, plates with screws, or a combination thereof.

15. A method according to claim 13, wherein the step of attaching the implant to the tissue is achieved by using screws.

16. An implant according to claim 1, wherein the mosaic plates are molded at intersections of wires which form the wire arms, the wire arms extend from sides of the mosaic plates, and the wire arms maintain the mosaic plates in relationship to each other.

17. An implant according to claim 1, wherein the wires form a dished shape.

18. An implant according to claim 1, further comprising screws for attaching the implant to tissue of a patient.

19. An implant according to claim 1, further comprising titanium plates and screws for attaching the implant to tissue of a patient.

20. An implant according to claim 1, wherein the wires form a dished shape and wherein at least some of the hexagonal shaped mosaic plates have slanted side walls whereby, in each plate having slanted side walls, a maximum width w of a top hexagonal-shaped surface of the plate is greater than a maximum width w of a bottom hexagonal-shaped surface of the plate.

* * * * *